United States Patent [19]

Weltz et al.

[11] Patent Number: 5,368,826
[45] Date of Patent: Nov. 29, 1994

[54] CONTROL APPARATUS FOR FLUID DISINFECTION MODULES AND SYSTEMS

[75] Inventors: Richard K. Weltz, Richmond; Peter Schuerch, Mechanicville, both of Va.

[73] Assignee: Infilco Degremont, Inc., Richmond, Va.

[21] Appl. No.: 986,119

[22] Filed: Dec. 4, 1992

[51] Int. Cl.⁵ .......................... A61L 2/00; C02F 1/32; G05B 13/00
[52] U.S. Cl. ....................... 422/243; 210/85; 210/748; 250/435; 250/436; 422/3; 422/23; 422/24
[58] Field of Search ............... 422/243, 2, 3, 22, 23, 422/24, 186.3; 210/748, 85; 250/432 R, 435, 438, 436

[56] References Cited

U.S. PATENT DOCUMENTS

| | | | |
|---|---|---|---|
| 3,182,193 | 5/1965 | Ellner et al. | 250/431 |
| 3,462,597 | 8/1969 | Young | 250/431 |
| 3,566,105 | 2/1971 | Wiltrat et al. | 250/435 |
| 3,948,772 | 4/1976 | Ellner | 210/96.1 |
| 4,017,734 | 4/1977 | Ross | 250/435 |
| 4,103,167 | 7/1978 | Ellner | 250/432 R |
| 4,204,956 | 5/1980 | Flaton | 422/24 |
| 4,336,223 | 6/1982 | Hillman | 422/24 |
| 4,400,270 | 8/1983 | Hillman | 422/24 |
| 4,482,809 | 11/1984 | Maarschalkerweerd | 250/435 |
| 4,757,205 | 7/1988 | Latel et al. | 422/24 |
| 4,899,056 | 2/1990 | Ellener | 250/432 R |
| 4,917,782 | 4/1990 | Davies | 210/748 |
| 5,019,256 | 5/1991 | Ifill et al. | 422/24 |

FOREIGN PATENT DOCUMENTS

| | | | |
|---|---|---|---|
| 3739966 | 6/1989 | Germany | 422/243 |

Primary Examiner—Robert J. Warden
Assistant Examiner—L. M. Crawford
Attorney, Agent, or Firm—Miller & Christenbury

[57] ABSTRACT

An ultraviolet fluid disinfection system including:
  one or more fluid flow passageways,
  one or more modules located in each passageway, each module having one or more rows of ultraviolet lamps, positioned to irradiate the fluid with ultraviolet,
  a lamp control assembly connected to each row of lamps to monitor data from and control operation of the lamps,
  a power distributor connected to the lamp control assemblies,
  a data interface connected to the lamp control assemblies, and
  a data control assemblies connected to the data interface and to the lamp control assemblies to read data from the lamp control assemblies and communicate with the data interface.

33 Claims, 11 Drawing Sheets

UV MODULE STATUS

Channel : 01
Bank : 03
Module : 2
Serial # : KA123W38

| | LCA1 | LCA2 | LCA3 | LCA4 | LCA5 | Lamp No. |
|---|---|---|---|---|---|---|
| | □ | □ | □ | □ | □ | 8 |
| | □ | □ | □ | □ | □ | 7 |
| PH1 | □ | □ | □ | □ | □ | 6 |
| | □ | □ | □ | □ | □ | 5 |
| DCA | □ | □ | □ | □ | □ | 4 |
| | □ | □ | □ | □ | □ | 3 |
| P=X | □ | □ | □ | □ | □ | 2 |
| | □ | □ | □ | □ | □ | 1 |
| Row | 1 | 2 | 3 | 4 | 5 | |

□ Preheat ON

*Fig. 11*

Channel : 01
Bank : 03
Module : 2
Serial # : KA123W38

UV MODULE STATUS

Lamp location is in Row 1, Lamp No. 6

Total hours    :    4685

Total cycles   :    31236

Status         :    Failed Lamp

Press ESC to continue

☐ Preheat ON

|     | LCA1 | LCA2 | LCA3 | LCA4 | LCA5 | Lamp No. |
| --- | --- | --- | --- | --- | --- | --- |
| PH  |     |     |     |     |     | 8 |
| 1   |     |     |     |     |     | 7 |
|     |     |     |     |     |     | 6 |
|     |     |     |     |     |     | 5 |
|     |     |     |     |     |     | 4 |
|     |     |     |     |     |     | 3 |
|     |     |     |     |     |     | 2 |
|     |     |     |     |     |     | 1 |
| Row | 1   | 2   | 3   | 4   | 5   |   |

*Fig. 12*

Disinfection System

Lamp Status Listing
(Failed Lamps only)

09/03/92        LSTAT-A

| Chnl # | Bnk # | Mod # | Lamp ID | Lamp Status | Hours | Cycles | Last Repl. |
|---|---|---|---|---|---|---|---|
| Module serial # is : | | | KA123W38 | | | | |
| 1 | 3 | 2 | 16 | Lamp Failure | 4,685 | 31,236 | 03/09/92 |
| | | | 55 | Lamp Failure | 8,630 | 57,532 | 09/27/91 |
| | | | 56 | Lamp Failure | 4,021 | 26,807 | 04/06/92 |
| Module serial # is : | | | KA123W55 | | | | |
| 1 | 5 | 1 | 31 | Lamp Failure | 9,107 | 60,711 | 09/07/91 |
| | | | 30 | Lamp Failure | 1,371 | 9,138 | 07/25/92 |

* End of Report *
Stack free : 2572

Lamp hours and Cycles for failed lamps

CONTROL APPARATUS FOR FLUID DISINFECTION MODULES AND SYSTEMS

FIELD OF THE INVENTION

The present invention relates to control apparatus for use in fluid disinfection modules and fluid disinfection systems, particularly to control apparatus for ultraviolet light producing modules and ultraviolet light waste water disinfection systems.

BACKGROUND OF THE INVENTION

Waste water disinfection systems utilizing ultraviolet (sometimes hereinafter "UV") treatment of waste water, such as industrial and municipal waste water, rely on complex systems presenting a wide variety of problems and challenges. The problems associated with such complex systems are enhanced in view of the wide span of engineering and scientific disciplines encountered, such as civil engineering, electrical engineering, computer hardware and software design, biology, chemistry and the like, in the design and construction of effective treatment systems. A representative example of some of the difficulties that have arisen in designing and constructing ultraviolet disinfection systems include a number of the items set forth below.

Radiation from ultraviolet light producing lamps utilized in UV disinfection systems decreases with time. There is typically a rapid drop in radiation during the first one hundred hours of operation. Following this initial period the decline in efficiency continues but at a much slower rate. After approximately 8800 hours of "on" service, or about one year of continuous operation, lamp efficiency drops to about 65% of its efficiency after the first 100 hours and typically no longer provides sufficient intensity to achieve the desired degree of disinfection. At this point to maintain operating efficiency of the system lamps are usually replaced.

Most UV installations replace lamps yearly to insure adequate waste water disinfection. Some lamps are replaced before they have been in "on" service a full year because not all lamp banks are in service during low flow periods. This typical mode of lamp replacement insures adequate disinfection but wastes the useful life of the lamps. This is an expensive and inefficient process in view of the many extra lamps purchased, the labor needed to monitor and change extra lamps and interrupted waste water treatment.

It is also known to employ relatively sophisticated control schemes to minimize electrical power consumption. In general, these schemes turn banks of lamps on and off in response to changes in waste water flow, which is constantly monitored. Using this mode of operation conserves both power and lamp life but, it introduces the additional factor of reduced filament life for the lamps because of the many "on-off" cycles. This is particularly true of plants fed by cycling pumps. A standard lamp has a filament life of 2000 to 3000 on-off cycles—after which time the lamp must be replaced.

The need to frequently replace lamps is further compounded by the problem that the lamps are submerged in a moving body of water, typically an open channel, which should remain continuously operational to maximize efficiency. Removing lamps or banks of lamps from the waste water flow can lead to significant efficiency losses due to water treatment stoppage, added personnel costs and the like.

It is also critical that the status of the UV lamps be continuously monitored to ensure that a proper dosage of ultraviolet radiation is produced for the waste water treatment process. Failure to maintain a proper dose of ultraviolet radiation can result in incomplete treatment, thereby permitting bacteria and other living organisms to escape in a live and active condition in the treated effluent. Of course, this is highly undesirable. It is therefore important that as much attention as possible be accorded to all ultraviolet radiation producing lamps to ensure proper dosage, while maintaining an efficient, low cost system.

Another aspect of maintaining proper ultraviolet radiation dosages relates to protective jackets that typically surround the ultraviolet lamps. These protective jackets become covered with particulate matter over the course of time, which reduces the UV radiation dosage to the waste water. A number of methods of cleaning these protective jackets are known. However, determining the frequency of the need for such cleaning and the efficiency of such cleaning is an important task that contributes to the total operating efficiency of the disinfection system.

Coordination of monitoring of the cleaning function with other operational functions such as waste water flow rate, waste water characteristics, ultraviolet radiation dosage, lamp life, lamp cycle life, electrical power requirements, personnel needs and the like, has proven to be a difficult task heretofore not completely mastered.

OBJECTS OF THE INVENTION

It is an object of the present invention to provide a comprehensive yet simple control apparatus for ultraviolet disinfection modules utilized in waste water disinfection systems.

It is another object of the present invention to provide control apparatus which comprehensively coordinates all operations of an ultraviolet waste water disinfection system.

It is an important object of the present invention to provide control apparatus for a waste water disinfection system and the modules used therein which permits fewer lamps replacements, reduced personnel requirements, minimal maintenance monitoring and curtailed electrical consumption.

Other objects and advantages of the present invention will become apparent to those skilled in the art from the drawings, the detailed description of preferred embodiments and the appended claims.

SUMMARY OF THE INVENTION

The present invention relates to an ultraviolet fluid disinfection system and includes one or more passageways through which fluids to be disinfected may flow. The system further includes one or more modules located in each passageway and positioned to contact the fluid. Each module has one or more banks of ultraviolet producing lamps and each bank contains one or more of the ultraviolet producing lamps. The system also includes one or more power and data distribution centers connected to the modules and one or more data and information interfaces connected to the modules. Also included are one or more lamp control assemblies which monitor and collect data from each lamp and controls operation of each lamp and one or more data control assemblies which read and store data from the lamp control assemblies.

The invention further includes an ultraviolet producing module for disinfecting fluids. The module includes one or more lamps capable of producing ultraviolet radiation and a housing connected to the lamps, wherein the housing is capable of receiving power from the power supply. The modules also include at least one lamp control assembly positioned in the housing to monitor data from the lamps and is capable of controlling operation of the laps. At least one data control assembly is positioned in the housing to read and store data from the lap control assembly(s) for storage in a memory in the modules, wherein the data control assembly is capable of connection to a remote computer or controller for receiving and transmitting information.

BRIEF DESCRIPTION OF THE DRAWINGS

FIG. 11 is a schematic of a display produced by the control apparatus of the invention.

FIG. 12 is a schematic of a display produced by the control apparatus of the invention.

FIG. 13 is a schematic of a display produced by the control apparatus of the invention.

DETAILED DESCRIPTION OF THE INVENTION

Figure 1:
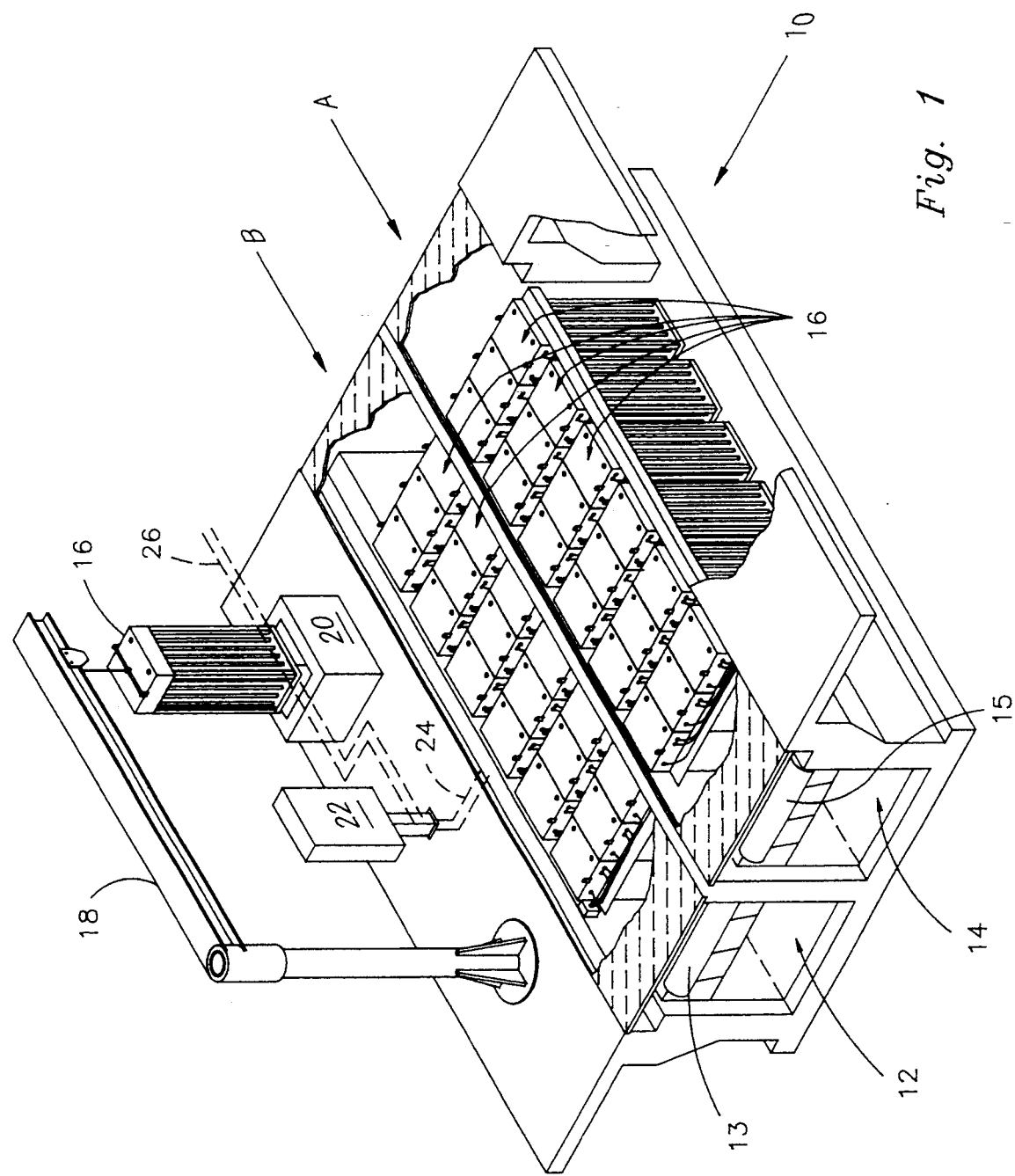
FIG. 1 shows a perspective schematic view of an ultraviolet light disinfection system in accordance with aspects of the invention.

It will be appreciated that the following description is intended to refer to the specific embodiments of the invention selected for illustration in the drawings and is not intended to define or to limit the invention, other than in the appended claims.

Turning now to the drawings in general and FIG. 1 in particular, the number 10 designates a waste water disinfection system. System 10 in the embodiment shown includes two waste water channels, 12 and 14, which are open channels having two side walls and a floor (not numbered). The level of waste water through channels 12 and 14 is controlled by gates 13 and 15, respectively, and preferably other gates not shown. A multiplicity of modules 16 are positioned in channels 12 and 14 in a series of six rows, each row having three modules aligned side by side. Modules 16 are portable and may be removed by crane 18, for example, and placed into a remotely located cleaning basin 20. Control panel 22 assists in operation of the overall disinfection system 10 and connects directly to modules 16 via connection 24 and to a remote control location (not shown) via connector 26. Waste water to be disinfected flows through channels 12 and 14 in the direction shown by arrows "A" and "B", although flow in either direction is possible.

Figure 4:
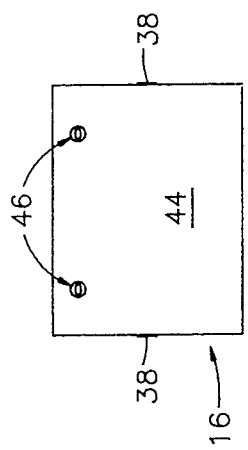
FIG. 4 is a schematic top plan view of the module shown in FIGS. 2 and 3.
Figure 3:
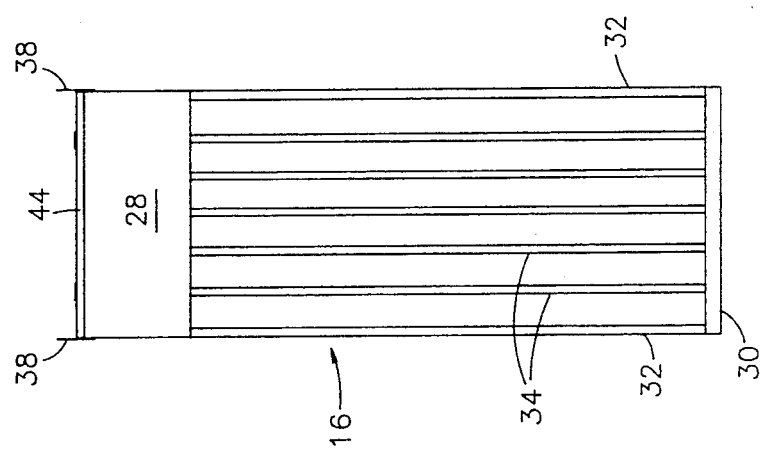
FIG. 3 is a schematic front elevational view of the module shown in FIG. 2.
Figure 2:
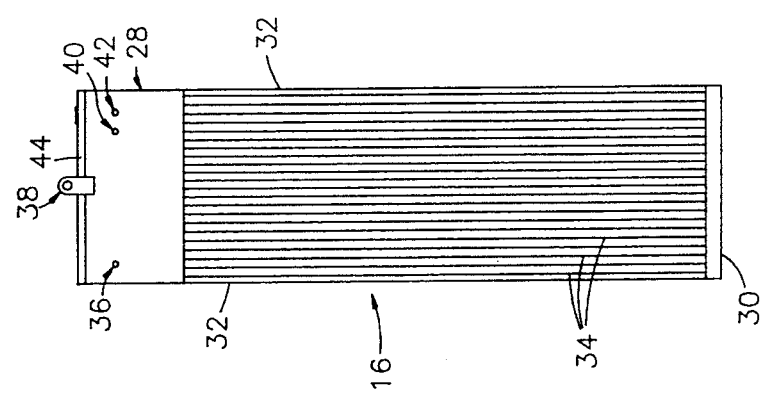
FIG. 2 is a schematic side elevational view of a module employed in a disinfection system of the invention.

Referring to FIGS. 2-4, module 16 is shown in an enlarged form for ease of understanding. Module 16 includes a housing 28, a lower header 30 and support legs 32. A multiplicity of ultraviolet lamps 34 connect between housing 28 and lower header 30. Housing 28 has a power connection fitting 36, suspension eyes 38, a data connection fitting 40 and an air source connection fitting 42. Housing 28 is enclosed on all sides and has a hinged cover 44, which may be opened and closed, and latched in place with latches 46.

Figure 5:
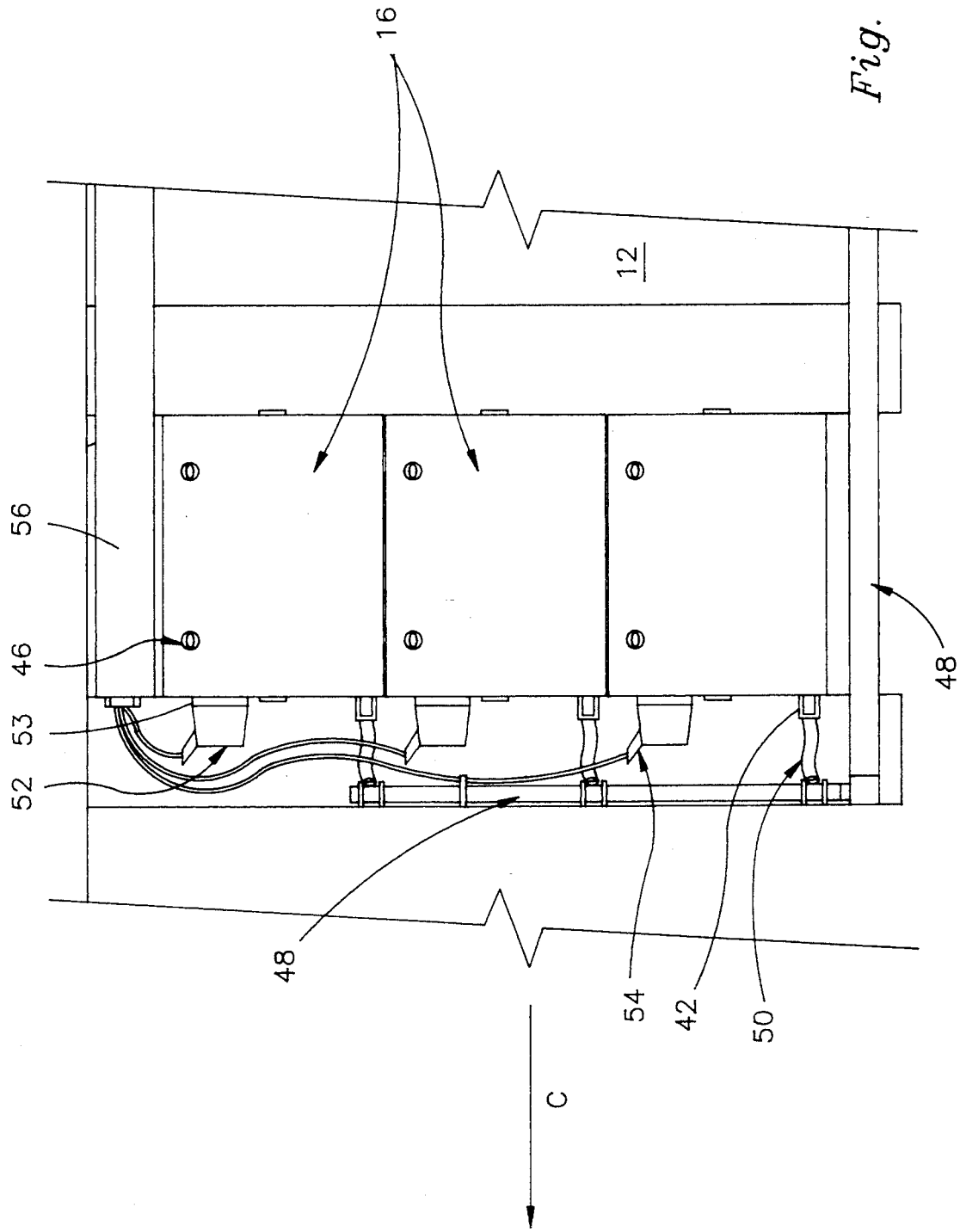
FIG. 5 is a schematic top plan view of a portion of an open channel and three modules used in the system shown in FIG. 1, exploded for ease of understanding.

FIG. 5 shows three modules 16 located within channel 12 (or 14) from a top plan view and connected to a lamp cleaning system and the control lines. Modules 16 are arranged side by side in a row, the direction of the row being perpendicular to the flow of waste water through the channel, which is shown by the arrow "C". Modules 16 are connected to an air supply line 48 via air connection hoses 50. Air supply line 48 connects to a pressurized source of air, which is well known and not shown. Fluids other than air, both gaseous and liquid, may be substituted for air, although air is preferred. Each air connection hose connects to air source connection fitting 42, which is mounted to housing 28 of module 16.

Quick disconnect connector 52 connects by snapping or plugging into receiver 53 onto the housing 28 of each module 16 and includes an interconnect cable 54 which extends through a protector conduit 56 which leads to control panel 22 of FIG. 1. Interconnect cable 54 contains both power and control lines for modules 16. In a most preferred embodiment, separate power and data cables are provided and are shown in FIG. 6 as separate connectors 36 and 40, respectively.

Figure 6:
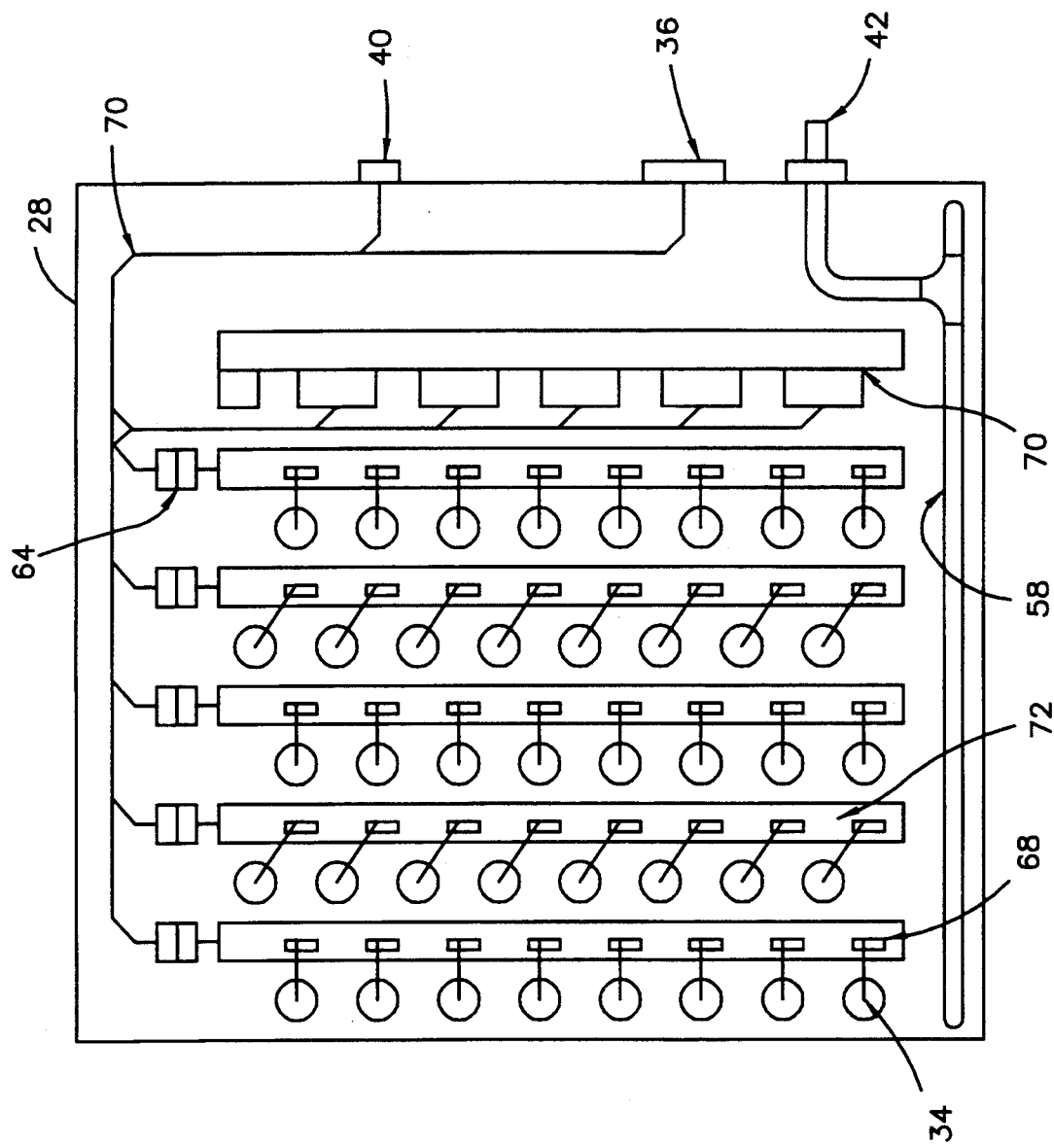
FIG. 6 shows a schematic top plan view of the interior of a module housing.

FIG. 6 schematically shows the interior of housing 28 and exterior fittings. Exteriorly of housing 28 is located air source connection fitting 42 (which connects to air source connection fitting 42 of FIG. 5), power connection fitting 36 and data connection fitting 40. Power connection fitting 36 and data connection fitting 40 may be located directly adjacent to one another or combined into one fitting, which can then engage quick disconnect connector 52 of FIG. 5. Air source connection fitting 42 connects to air scrub feed tube 58 which connects to further piping or conduit (not shown) extending downwardly toward lower header 30 of FIGS. 2-4. Wiring harness 60 connects power connection fitting 36 and data connection fitting 40 to data control assembly (DCA) 70 and to ballast assembly power and logic connector 64. Each ballast assembly power and logic connector 64 connects directly to a lamp control assembly (LCA) 72, which connects to and contains ballasts. In turn, each LCA 72 connects to a lamp connector 68 which in turn connects to lamps 34.

Figure 7:
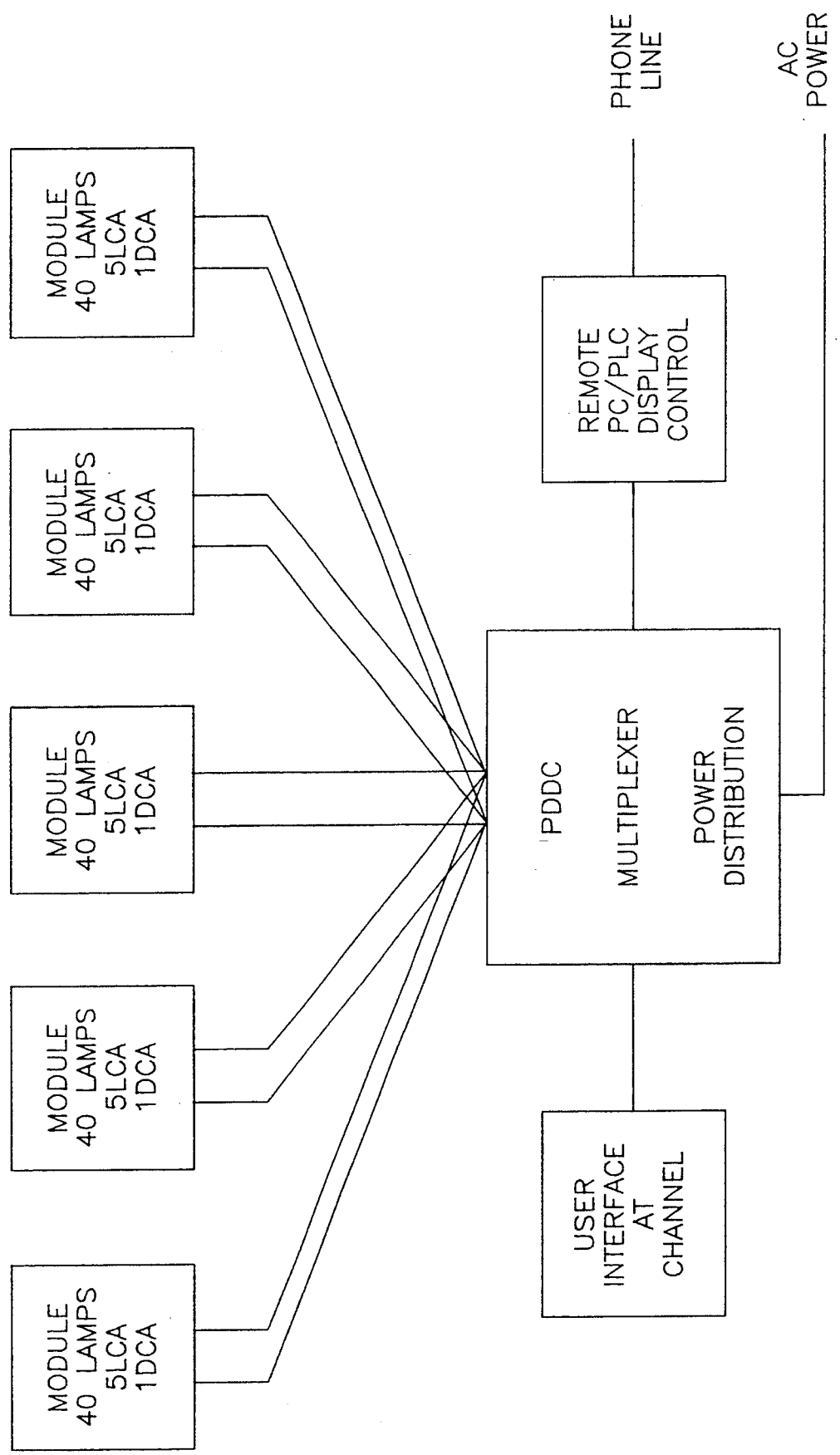
FIG. 7 is a block diagram of the disinfection system of the invention.

FIG. 7 shows a block diagram of an especially preferred embodiment of a disinfection system of the invention. The array of modules located at the top of FIG. 7 represents modules 16 placed within a channel 12 or 14 and connected to a power distribution data center (PDDC). Each module 16 includes forty lamps in five rows of eight lamps. Each row connects to a lamp control assembly (LCA) 72 and each module has a data control assembly (DCA) 70. The power distribution data control center (PDDC) connects to a user interface located at or proximate to the channel, such as at control panel 22, and further may be connected to a remotely located personal computer or programmable logic controller. The personal computer or programmable logic controller also preferably connects to a phone line for modem type communications. The entire system is connected to an AC power source.

Figure 8:
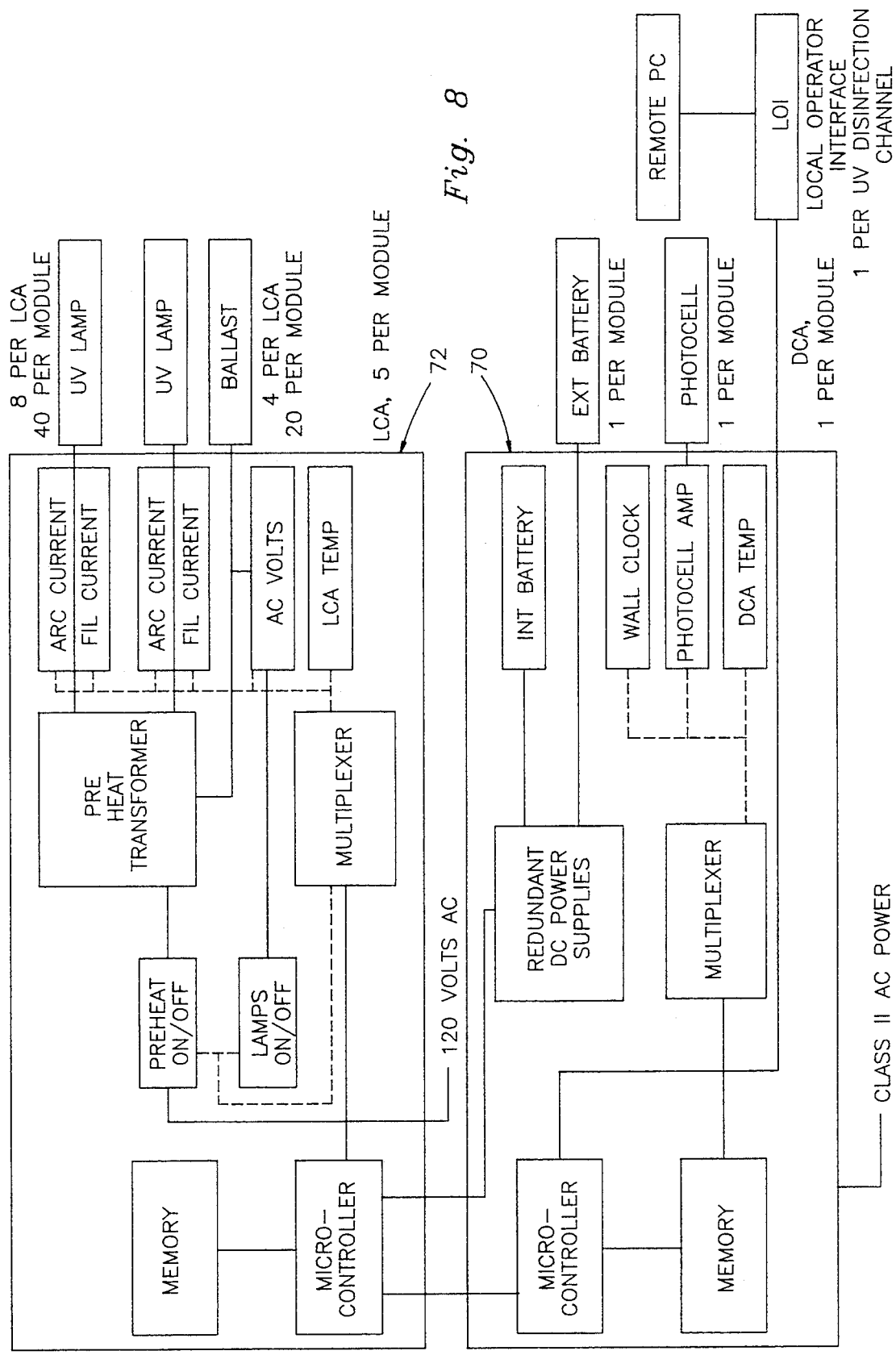
FIG. 8 is a block diagram of a lamp and data control assembly of the invention.

FIG. 8 illustrates (schematically) a further aspect of the system wherein ultraviolet sensitive photocells are located within channel 12 or 14 and detect ultraviolet radiating from lamps 34. The installation and operation of such photocells is known in the art. The intensity of the ultraviolet radiation is monitored and a signal is sent to the DCA which connects to control panel 22. The ultraviolet light intensity reading may be displayed on a display panel, such as control panel 22, or on a remotely located computer display. One photocell is shown connected to each module, although variations in the number and position of photocells are known.

FIG. 8 further illustrates a preferred embodiment of the invention for monitoring and control of an ultraviolet disinfection system. A command signal may be generated in the local operator interface, such as a control panel 22, from an external source such as a central computer. This signal is then sent to a DCA 70 microcontroller which accesses the DCA 70 memory for its current status and then sends the appropriate command signal to the LCA 72 microcontroller. The microcontroller in LCA 72 then accesses the LCA for its current status and sends the appropriate command signal to the multiplexer in LCA 72. The command signal is then relayed by the multiplexer to the preheat or lamp control, changing the off/on status of the preheat transformer or lamps 34 accordingly.

A monitoring signal generated in the arc current, filament current, AC voltage and LCA 72 temperature monitors is sent to the LCA 22 multiplexer which relays the signals to the LCA 72 microcontroller. The microcontroller in LCA 72 then sends these signals to the DCA 70 microcontroller, which then accesses the DCA 70 memory for its current status and sends the appropriate command signal back to the LCA 72 microcontroller. The DCA 70 microcontroller also sends the appropriate signal to the local operator interface. Wall clock, photocell and DCA 70 temperature monitoring signals are generated in these respective monitors and sent to the DCA 70 multiplexer, which then relays these signals to the DCA 70 memory for access by the DCA 70 microcontroller.

Figure 9:
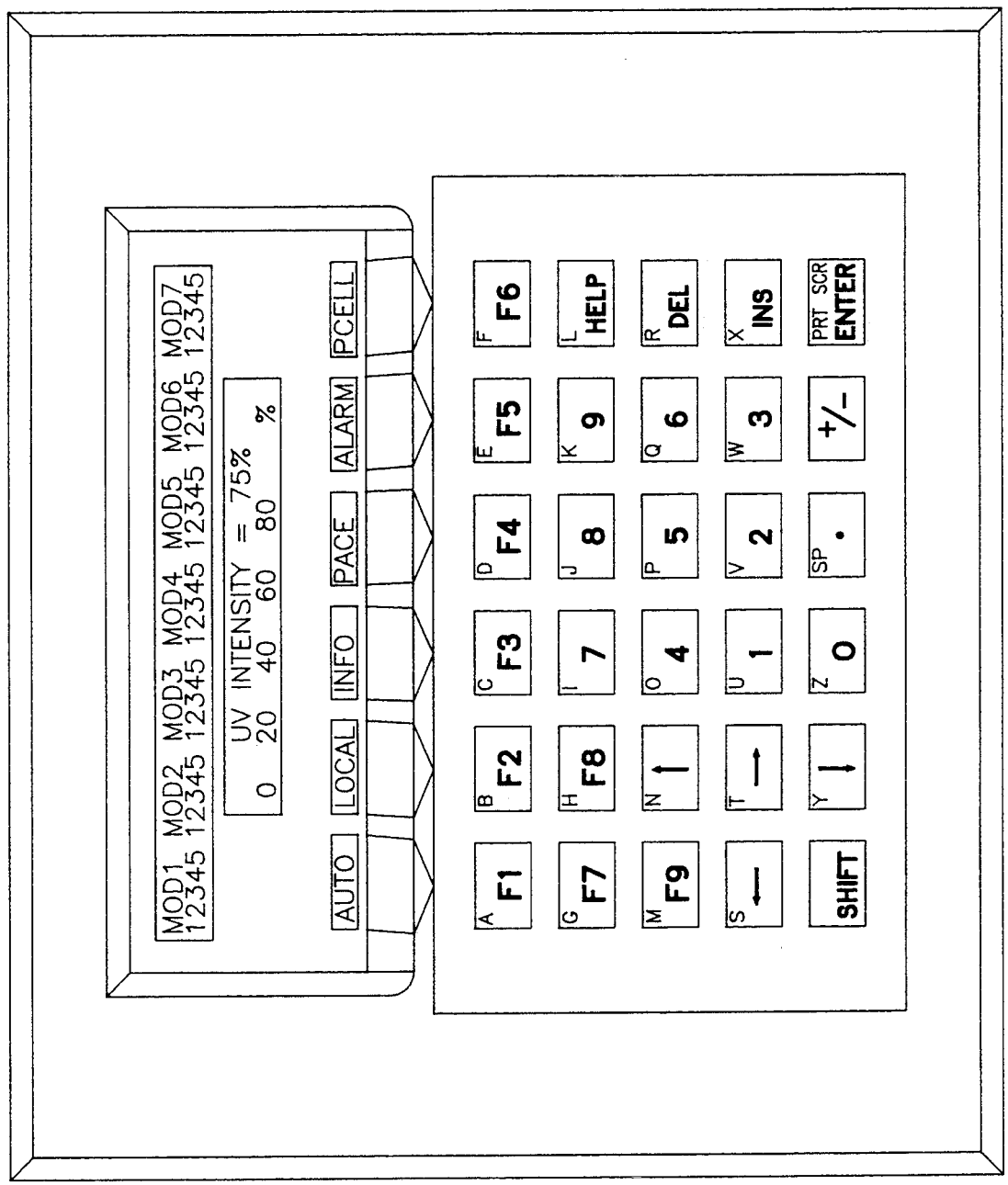
FIG. 9 is a schematic of a display produced by the control apparatus of the invention.

FIG. 9 shows a readout from a display such as that located on control panel 22 of FIG. 1. The display includes a keypad to input data as well as commands and queries for the system. The upper and middle portions of the display include horizontal bar graphs for displaying relevant information. The upper graph displays modules and rows of lamps in operation, while the middle portion indicates UV intensity.

Figure 10:
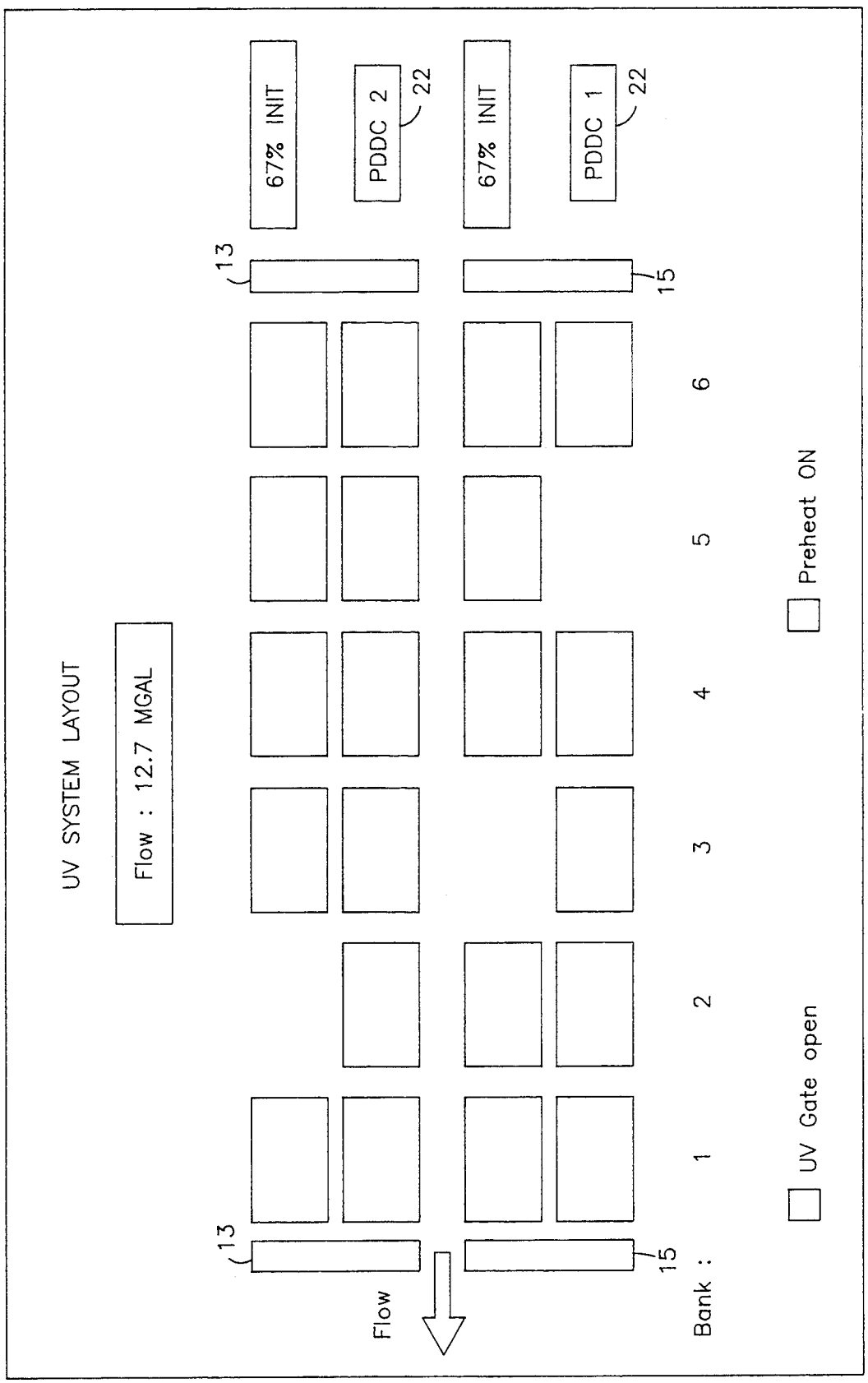
FIG. 10 is a schematic of a display produced by the control apparatus of the invention.

FIG. 10 shows a display of a schematic of the system on the screen of a connected computer, wherein rectangular boxes represent modules located within a channel. Other information such as waste water flow rate, waste water flow direction, the number of module rows and the like is displayed.

FIG. 11 shows a similar display which represents one module within a channel and the respective lamps contained within the module, by location. In the particular embodiment shown there are eight lamps located in five rows.

FIG. 12 also shows a display which provides information concerning a particular lamp at a particular location and its status.

FIG. 13 shows still a further display which provides particularized information with respect to a number of modules located within a channel and the status of lamps within the modules.

Operation of the system of the invention will now be described below.

Control of one preferred embodiment of the system is carried out adjacent to channels 12 and 14 as shown in FIG. 1. A power distribution data center (PDDC) or control panel 22 is located adjacent to channels 12 and 14 and is used to distribute incoming electric power to each of modules 16 and to receive data from the data control assemblies (DCAs) 70 mounted in individual modules 16. Access to this information is gained through the local operator interface which is mounted on control panel 22.

The local operator interface is preferably a microprocessor based data unit with keyboard access and a rear illuminated liquid crystal alphanumeric display. Normally the system operates in a fully automatic mode and the local operator interface displays the information shown in FIG. 9.

Control panel 22 most preferably consists of a free standing weather proof stainless steel electrical enclosure that has a local operator interface mounted to be accessible without opening of the electrical enclosure, one or two circuit breaker load centers and any optional equipment. One control panel 22 should be employed for each UV disinfection channel of the UV disinfection system. All electrical cabling for a UV disinfection channel should preferably connect to and radiate from one control panel 22.

The local operator interface makes it quick and easy to set up and operate system 10. The local operator interface provides channel side control by the system operator for the system. With the local operator interface an operator can view operating parameters, alarm conditions, and set all variable operating parameters at one location. Some of the especially preferred features of the local operator interface are:

high contrast back-lit liquid crystal display (LCD) with graphics;
waterproof keypad with software assigned keys, program key functions plus "HELP";
field replacement battery to back up the operating program and all critical system information;
"LOCKED" program, cannot be listed, viewed, or changed from the local operator interface;
monitoring circuitry to safeguard memory contents;
fully automatic restart of system after a power outage;
signal and data inputs and outputs are optically isolated; and
electromagnetic interference (EMI) proof circuitry, allows operation in EMI environments.

Whenever the local operator interface is powered, an AUTO display screen displays two bar graphs, which is the AUTO screen. The top bar graph shows the number of modules 16 and number of rows of UV lamps 34 within the modules that should be operating as called for by either the waste water flow pace system (which monitors waste water flow rates) or the system operator. The bottom bar graph shows the UV intensity measured by a UV sensitive photocell.

Also on the AUTO screen Just below the two bar graphs are preferably a row of soft key labels; AUTO, LOCAL, INFO, PACE, ALARM, and PCELL that correspond to and are aligned with the local operator interface soft function keys F1 through F6 immediately below on the operator key board. These soft key labels can change as different screens are displayed and assign different soft key functions to the local operator interface soft function keys F1 through F6.

In addition to the soft function keys F1 through F6 there are most preferably the following active keys:
HELP, the help key presents the operator with on screen help for certain functions;
ENTER, the enter key is used when entering operator selected or determined numeric values;
DEL, used to delete a numeric value entered by mistake; and
the numeric keys 0 through 9 and decimal point, are used when entering operator selected or determined numeric values.

Whenever a soft key (F1 through F6) is pressed that shifts out of the AUTO screen an internal timer is preferably started that automatically returns the system to the AUTO screen after a delay of twenty-five (25) seconds.

A delay preferably occurs between the time a soft function key is pressed and the time that the soft function is executed. This occurs because of the time it takes the local operator interface to poll all of modules 16 for current data and at what point in the continuous polling cycle the soft function key was pressed.

The back light for the LCD display screen preferably turns off automatically when ten (10) minutes after the last press of soft key F1. To reactivate the back light the soft function key F1 should be pressed and held until the back light turns on, from one half to five (5) seconds. If the display screen is alternating between the AUTO dual bar graph display and the ALARM display then there is an alarm condition pending. If there is more than one alarm, the number of alarm conditions are conducted by the number of times the ALARM system flashes. This allows the system operator to quickly, from a distance, determine the number of alarm conditions existing.

The back light for the LCD display is preferably automatically activated whenever an alarm condition exists. To determine the cause of an alarm condition or conditions the soft key ALARM (F5) should be pressed and the screen displays a list of pending alarms. From within the ALARM screen the system operator may return to the AUTO screen or go to the LOCAL screen by pressing the appropriate soft key.

If the flow pace system is turned off the LOCAL screen preferably allows the system operator to manually select the number of modules and number of UV lamps within the modules that are operating. After the system operator has made a selection, it is stored in a battery backed memory and the local operator interface may be switched back to the AUTO screen. The system uses the operator selection for the number of modules and number of rows of UV lamps operating. The operator selection .preferably cancels after twenty-five seconds when the flow pace system is operating. The flow pace system responds to a 4 to 20 milliamperes signal or other analog or digital signal from the treatment plant effluent flow meter and automatically adjusts the number of modules and number of rows of UV lamps within the modules that are in operation.

The PACE screen allows the system operator to manually turn the flow pace system on or off. When the flow pace system is turned off the number of modules and number of rows of UV lamps within the modules that are operating are set by the system operator using the LOCAL screen. From within the PACE screen the system operator may return to the AUTO screen or go to the COEF screen. The COEF screen allows the system operator to enter the flow coefficient to be used by the flow pace system. When using the COEF screen pressing the HELP key brings up a help screen for this function. The flow coefficient is equal to the peak disinfection flow rate times the quantity of 16 divided by the flow meter rate represented by 20 milliamperes.

$$\text{Peak Disinfection Flow Rate} \times \frac{16}{\text{Flow Meter Rate Represented by 20 Milliamperes}}$$

The INFO screen allows the system operator access to various system operating data. From within the INFO screen the system operator may return to the AUTO screen or go to the FLOW, TEMP, or MODULE screens by pressing the appropriate soft key. The FLOW screen allows the operator to view system flow, as determined by the flow pace system, as a percent of the peak UV disinfection flow. The TEMP screen allows the operator to identify abnormal temperature conditions within any selected module.

The MODULE screen allows the operator to view individual UV lamp operating hours and total off/on cycles within any selected module. The PCELL screen displays the last UV intensity reading and allows the system operator to enter PICK and CAL screens. The PICK screen allows the system operator to select the UV sensitive photocell that will be displayed on the UV intensity bar graph on the AUTO screen.

If the selected UV sensitive photocell has been replaced after initial installation, the CAL screen allows the system operator to enter HT and LT calibration values provided with the replacement UV sensitive photocell. High transmission (HT) and low transmission (LT) calibration values refer to the HT and LT values recorded on a calibration tag attached to the electrical connector attached to the UV sensitive photocell. The HT and LT calibration values restored in battery backed memory within the data control assembly (DCA) 70 of the module in which it is located.

Control panel 22 contains either one or two circuit breaker load centers depending on the nun%bet of modules installed in the UV disinfection channel. Each circuit breaker load center contains a main circuit breaker, control circuit breaker, and individual ground fault circuit interrupter circuit breakers, also called equipment protection device (EPD) ground fault circuit interrupters.

Operation of the local operator interface results in the screens shown in FIGS. 9-13. Referring to FIG. 9, the upper portion of the display, preferably through the use of a horizontal bar graph shows the number of modules 10 in service and the number of rows of lamps 34 within the last module which are in service. Information which is used to determine the number of lamps 34 in service is received from a plant effluent flow meter, the form and installation of which is known in the art.

The middle portion of the display, again preferably in the form of a horizontal bar graph, displays UV intensity from one of modules 16 which has been selected as a control unit. An actual number is also preferably displayed.

The lower portion of the display identifies which of the function keys can be used to access or change the display. In FIG. 9, F1 allows the operator to switch from automatic to hand control, F2 allows local control of lamps 34 should the operator wish to adjust the number of lamps 34 in service. F3 allows the operator access to other system information such as channel flow and individual module 16 status. F4 accesses the information provided by the flow pacing system. In the event of an alarm condition, such as a lamp failure, for example, F5 allows the operator to find the exact alarm condition and to identify the exact component requiring attention. Finally, F6 allows the operator to check UV intensity in other modules 16 and to change which of modules 16 is the control module for UV intensity monitoring.

Should an alarm occur, the display automatically changes from that shown in FIG. 9 to visually indicate the alarm. It can also be accompanied by an audible signal. In such case F5 is selected and the alphanumeric display advises the operator of the reason for the alarm and identifies the component requiring attention. Under local control the display changes and the operator is able to use F3, F4 and F5 to decrease or increase the number of lamps 34 in use or, if required, switch on all of lamps 34 in channel 12 or 14.

An especially preferred control and monitoring system 10 of the invention includes the system already described above with the addition of a full computer based system.

The expanded system works essentially the same as previously discussed but communicates directly with a computer. System software gives full monitoring and control, from a remote location, and adds many other advantageous features over the prior art. Several particularly advantageous features include graphic representation of system condition and accumulated data, input of external data such as fecal coilform, suspended solids and BOD results, and control of other flow related controls such as motorized gates 13 and 15, and other gates not shown, for example.

The system most preferably utilizes pull down menu screens to provide for greatly enhanced ease of operation. When running in an automatic mode system 10 displays a graphic representation of the channels as shown in FIG. 10. The screen in FIG. 10 shows all equipment in channels 12 and 14 plus other related items such as upstream and downstream gates and the control panels 22. Current waste water flow and the individual channel UV intensities are also continuously displayed and updated.

In an especially preferred form shown in FIG. 10, the system provides modules 16 shown in a green color on the screen represent modules in use, those shown in a yellow color are not in use but are under pre-heat conditions so that they may be brought into use as soon as the plant's effluent flow meter signals that they are needed. Modules 16 shown in a gray color are not in use at all, possibly meaning that they have been withdrawn for cleaning. Finally, a module 16 shown in a red color means that an alarm in this module has been initiated. Gates shown in a green color are open, those shown in a gray color are closed.

In the event of an alarm, the operator, preferably using either a mouse or computer cursor keys, can select the offending module 16 and display it on the screen for closer investigation. A new screen is selected either by clicking the mouse or by using the "enter" key and is shown in FIG. 11. In the screen shown in FIG. 11, a plan view of module 16 is shown with UV lamps 34 depicted in the same geometric pattern as they are in the module. Five LCAs 72 are shown, one for each row of eight lamps 34. A power supply and photo cell status are also indicated along with DCA 70.

As with the previous screen, lamps 34 in use are most preferably shown in a green color and alarms are shown in a red color. Since system 10 has the ability to flow pace by row of lamps within the module, those lamps not in use but waiting are shown in a yellow color. Lamps 34 and any of the supporting controls can register an alarm and are shown up in a red color. With the use of the mouse or the cursors the problem component can be isolated and investigated with an on screen status display. In such case, the lamp shown in a red color is selected and the lamp's current status in terms of hours of use, number of times it has switched on and off and the fact that it has now failed is shown. The lamp's exact location is given so that it may be easily found and replaced by maintenance personnel. This is shown in FIG. 12.

This novel method of investigation isolates problems very precisely and since every component is designed to be field serviced with the module remaining in its operating position it is a simple matter to direct maintenance personnel to the exact location with the necessary spare component for replacement. When such maintenance is carried out the DCA 70 can record the event and maintain the information in memory for later use. One such screen is shown in FIG. 13. FIG. 13 shows the lamp status in each of the modules 16 of those lamps 34 that have failed and been replaced. The record also shows the elapsed time and switching cycles that the lamp accumulated up to the time of its failure. This means that all lamps can be fully utilized up to their maximum for the first time.

As shown in FIG. 13 the module serial number shown is unique to the module and ensures that the data for that module will be maintained regardless of possible relocation within disinfecting channels 12 and 14. Other parameters are also recorded with the preferred system either via module mounted DCAs 70 or from remote sources such as an effluent flow meter or from manual data entry such as regular fecal coilform results.

The data is preferably accessed, by the operator, from the pull down menus in the system and can be depicted for selected periods of time such as last twenty four hours, thirty days or last sixty days. Graphical representation of the information can be shown on the screen or it can be down loaded to a printer so that the data can be used to support normal reporting procedures.

Various functions and features of two embodiments of the invention, one utilizing an local operator interface only and the other also employing a computer, as described below.

Each module 16 most preferably contains one DCA 70. Components of DCA 70 are preferably mounted on a removable fully encapsulated printed circuit board assembly. Each DCA 70 monitors and controls up to five LCA's 72. Logged data is logged and stored in a data file within DCA 70 and maintained by redundant DC power supplies and redundant battery backup systems. The following is a preferred list of DCA 70 monitor and control functions:

Generate a DCA 70 identification number from an EPROM;

Measure UV lamp arc current, eight for each of five LCA's 72;

Ignore UV lamp current readings during the first 10 minutes after turning on UV lamps 34;

UV lamp current in the normal range is averaged and logged as normal UV lamp operating hours;

Abnormal, low or high, UV lamp current is not averaged and logged as a UV lamp out condition;

If two (2) adjacent UV lamps and or greater than 15 percent of the UV lamps are logged as UV lamps out, a critical UV lamp out alarm is logged;

If any UV lamp operating hours exceeds a preset value, usually 8,760 hours, the end of UV lamp operating hours life is logged;

Log the number of Off/On cycles of each UV lamp;

If a UV lamp Off/On cycles exceeds a preset value, usually 100,000 cycles, the end of UV lamp cycle life is logged;

UV lamp filament condition is logged as filament failure if filament is open;

ELC operation is logged as a failure if it has failed;

ELC supply power is logged as a failure if present when UV lamps are off, logged as a failure if not present when UV lamps are on;

Logic circuit DC power supply monitor, one for each of two redundant DC power supplies, is logged as failure if it has failed;

Temperature, one for each of one DCA 70 and five for LCA's 72;

Temperatures in the range of 0 to 80 degrees C. for both DCA 70 and LCA's 72 are averaged and logged as normal operating temperature;

Temperatures in the range of 70 to 80 degrees C. for both DCA 70 and LCA's 72 are logged as a caution temperature, system operator to schedule equipment check;

Temperatures in the range of 80 to 85 degrees C. for both DCA 70 and LCA's 72 are logged as a hazardous temperature, system operator to check equipment now;

Temperatures greater than 85 degrees C. for LCA 72 are logged as a failure temperature and UV lamps 34 controlled by LCA 72 with the failure temperature condition are automatically turned off by DCA 70;

Temperatures greater than 85 degrees C. for DCA 70 are logged as a failure temperature and UV lamps 34 controlled by the DCA 72 are turned off;

When a row of UV lamps is turned off by DCA 70, an additional lamp row is turned on by the DCA 70 if possible;

If any module 16 is turned off by DCA 70 an additional module 16 is turned on by the central computer, if possible, if the central computer option is installed;

Zero to one hundred percent UV intensity photocell signal;

Ignore UV photocell signal during the first 10 minutes after turn on of the first row of UV lamps 34 in a module;

UV intensity is averaged and logged as UV intensity;

UV intensity below twenty-five (25) percent is logged as UV intensity failure;

UV intensity below fifty (50) percent causes the central computer to call for system cleaning;

UV lamp row Off/On control;

Default condition for all UV lamp rows is ON;

Each of five UV lamps rows within a module turned off by DCA 70 under direction of a LOI 22 in response to a signal from the plant effluent flow meter or local operator input; and LOI 22 responds to the plant effluent flow meter via the central computer.

Each module 16 most preferably contains five LCA's 72. Components of LCA's 72 are most preferably mounted on a removable fully encapsulated printed circuit board assembly. Each LCA 72 most preferably controls four ELC's that operate eight UV lamps 34 and four UV lamp filament preheat transformers via eight solid state relays. The following is a preferred listing of LCA monitor and control functions:

UV lamp current, 0 to 0.5 Amps AC (0.250 to 0.350 Amps AC=normal UV lamp current. Less than 0.250 Amps AC=abnormal low UV lamp current. Greater than 0.350 AC=abnormal high UV lamp current);

UV lamp filament monitor, each monitors two filaments (2 filaments open. 1 filament open, 1 filament good. 2 filaments good).

ELC operating signal, ELC operating, ELC not operating;

ELC 120 volt supply power, ELC supply power present, ELC supply power not present;

Temperature of LCA 72 microprocessor circuit board assembly, 0 to 100 degrees C.;

Temperature range of 0 to 80 degrees C.=safe temperature;

Temperature range of 70 to 80 degrees C.=caution temperature range;

Temperature range of 80 to 85 degrees C.=hazardous temperature, check equipment now;

Temperatures greater than 85 degrees C=failure temperature, automatic turn off of UV lamps;

UV lamps Off/On control (The UV lamps and preheat are controlled by signals from the DCA 70); and The default condition is UV lamps on and UV lamp preheat off from within the LCA 72 when ever the DCA 70 is not present.

The preferred vertical design of modules 16 reduces maintenance time and costs, increases system efficiency and increases worker safety in the operation of an effective UV disinfection system. All electrical wiring is located in the top of the module, above the waste water level, thereby avoiding hazardous underwater high voltage connections. Individual lamps 34 are also easily accessible from the top of the modules 16, allowing lamps 34 to be removed and replaced rapidly without interrupting disinfection. There is no need to remove and disassemble an entire module 16 to change a single lamp 34.

With vertical lamp positioning, protective Jacket coating build-up is less rapid, resulting in less frequent cleaning. When cleaning is required, two methods are available—an in-place chemical cleaning system that utilizes a split channel configuration to allow uninterrupted flow during the cleaning cycle and a permanent cleaning basin 20. Basin 20 is a special cleaning tank designed to hold one or more UV modules 16 at a time. Modules 16 can be removed individually from channel 12 or 14, then cleaned in basin 20 and returned to the system. Both methods include an air scour, in which compressed air is most preferably used to create a scrubbing dynamic in a cleaning solution that promotes greater surface friction and faster more efficient coating removal.

Although there is a watertight connection between the top of housing 28 of the module 16 and the quartz tubes surrounding lamps 34, its main purpose is to prevent water from entering housing 28 in the event channels 12 or 14 flood. During normal operation the water level in the channel is approximately six inches below the bottom of housing 28. The quartz connector can be loosened, a new jacket inserted, and the jacket replaced without removing module 16 from the channel.

Modules 16 preferably incorporate plug in potted printed circuit boards and lamps 34. Both may be removed and replaced in the channel through the modules 16 top cover 44. It is not necessary to remove module 16 from the channel. There are no "below water level" electrical connectors.

Modules 16 monitor and log the actual operating time of each lamp 34 in its given location in the module. Knowing the hours in actual service, it is possible to predict and schedule lamp replacement at the end of the useful life of the lamp instead of employing the prior arbitrary and wasteful technique. As the current cost of a replacement lamp is about U.S. $50, making it possible to easily utilize the full life of a lamp produces a significant savings.

Modules 16 are most preferably provided with "preheat transformers". These maintain a continuous filament current effectively eliminating the "off" condition of lamps 34. As an additional assurance of extended lamp life, "multi-cycle" lamps are most preferably used. The special filament construction of these amps provide a life of over 100,000 cycles.

Although this invention has been described in connection with the specific forms thereof, it will be appreciated that a wide array of equivalents may be substituted for the specific elements shown and described herein, and that a wide array of equivalents may be substituted for the specific steps described herein without departing from the spirit and scope of this invention as described in the appended claims.

What is claimed is:

1. An ultraviolet fluid disinfection system comprising:
   one or more fluid flow passageways;
   one or more immersible modules located in each passageway, each module having one or more ultraviolet producing lamps positioned to irradiate said fluid with ultraviolet;
   one or more lamp control assemblies connected to said lamps to monitor data from and control operation of said lamps;
   one or more power distributors connected to said lamp control assemblies;
   one or more data control assemblies connected to said lamp control assemblies to read data from said lamp control assemblies; and
   one or more data interfaces connected to said data control assemblies to communicate with said data control assemblies.

2. The system defined in claim 1 wherein said lamp and data control assemblies are positioned in said modules.

3. The system defined in claim 2 wherein each passageway and the modules located therein connect to one of said power distributors and one of said data interfaces.

4. The system defined in claim 1 wherein said lamp and data control assemblies are integral.

5. The system defined in claim 4 wherein said lamp and data control assemblies are positioned in said modules.

6. The system defined in claim 1 wherein said power distributors and data interfaces are positioned adjacent said passageways.

7. The system defined in claim 1 wherein said interfaces permit entry of commands for and/or queries to said data control assemblies and/or receipt of data or information from said data control assemblies.

8. The system defined in claim 1 wherein said interfaces are capable of receiving commands and/or queries from a remotely located computer or programmable logical controller.

9. The system defined in claim 1 wherein said system is capable of monitoring information or data selected from the group consisting of: status of UV lamps, number of UV lamps out, UV lamp filament condition, lamp control, automatic fail safe conditions, waste water flow rate past a row of UV lamps, all historic data stored in a data control assembly, individual module identification and ground fault condition for said modules.

10. The system defined in claim 1 wherein said interfaces are capable of displaying information or data selected from the group consisting of: the number of operating modules in said passageways, the number of operating lamps, the value of UV light intensity in said passageways, failure of UV intensity in said passageways, the number of alarm conditions in the system, the cause of an alarm in the system, the location of an alarm in the system; waste water flow rate in said passageways, individual lamp operating hours, number of individual lamp off/or cycles, individual lamp hours indicating end of life, individual lamp cycles indicating end of life, logic and control DC power failure, high temperature of lamp control assemblies, hazardous temperature of lamp control assemblies, high temperature of data control assemblies and hazardous temperature of data control assemblies.

11. The system defined in claim 1 further comprising a computer or a programmable logic controller connected to each of said interfaces.

12. The system defined in claim 11 wherein said interfaces are capable of displaying information or data selected from the group consisting of: number of adjacent failed UV lamps, percentage of failed IV lamps, UV lamp current, average UV current, UV lamp low/high current, failure of UV in the intensity modules, low UV intensity modules, temperature of said lamp control assemblies, temperature of said data control assemblies, module running time and individual module location.

13. The system defined in claim 11 wherein said computer is capable of displaying information or data selected from the group consisting of: number of adjacent failed UV lamps, percentage of failed UV lamps, UV lamp current, average UV lamp current, UV lamp low/high current, failure of UV in the intensity modules, low UV intensity modules, temperature of said lamp control assemblies, temperature of said data control assemblies, module running time and individual module location.

14. The system defined in claim 11 wherein said system is capable of performing functions selected from the group consisting of monitoring electronic lamp control, automatic controlling of passageway inlet gates, automatic controlling of passageway outlet gates.

15. The system defined in claim 1 further comprising one or more electronic lamp controllers or ballasts connected to said lamps.

16. The system defined in claim 1 wherein each module contains one or more data control assemblies.

17. The system defined in claim 1 wherein each module contains at least one row of lamps.

18. The system defined in claim 17 wherein each row of lamps is connected to one or more lamp control assemblies.

19. An ultraviolet fluid disinfection system comprising:
one or more fluid flow passageways;
one or more immersible modules located in each passageway, each module having one or more rows of ultraviolet lamps, positioned to irradiate the fluid with ultraviolet;
a lamp control assembly connected to each row of said lamps to monitor data from and control operation of said lamps;
a power distributor connected to said lamp control assemblies;
a data control assembly connected to said lamp control assemblies to read data from said lamp control assemblies; and
a data interface connected to said data control assemblies to communicate with said data control assemblies.

20. An ultraviolet producing immersible module for disinfecting fluids passing through a fluid passageway comprising:
one or more lamps capable of producing ultraviolet radiation;
a housing connected to said lamps, said housing capable of receiving power from a power supply for said lamps;
one or more lamp control assemblies positioned in said housing and connected to said lamps to monitor data from said lamps and being capable of controlling operation of said lamps; and
one or more data control assemblies positioned in said housing to read data from said lamp control assembly for storage in a memory, said data control assembly being capable of connection to a remote computer or controller for receiving and transmitting information.

21. The module defined in claim 20 wherein said lamp control and data control assemblies snap or plug into said housing.

22. The module defined in claim 20 wherein said lamp control and data control assemblies are integral.

23. The module defined in claim 20 further comprising one or more electronic lamp controllers or ballasts connected to said lamps.

24. An immersible fluid disinfection module comprising:
at least one lamp capable of producing ultraviolet radiation;
a housing connected to said lamp, said housing capable of receiving power from a power supply for said lamp;
a lamp control assembly positioned in said housing and connected to said lamp to monitor data from and control operation of said lamp, said lamp control assembly including a micro-controller, a memory, a multiplexer and a lamp on/off switch; and
a data control assembly positioned in said housing and connected to said lamp control assembly to read data from said lamp control assembly, said data control assembly including a micro-controller, a memory and a multiplexer, and capable of connection to a remote computer or controller for receiving and transmitting information.

25. The module defined in claim 24 wherein said lamp control assembly further comprises a lamp filament preheat transformer and preheat on/off switch.

26. The module defined in claim 24 wherein said lamp control assembly further comprises means for measuring the temperature of said lamp control assembly.

27. The module defined in claim 24 wherein said lamp control assembly further comprises means for measuring current to said lamp.

28. The module defined in claim 24 wherein said lamp control assembly further comprises means for measuring alternating current voltage in said lamp.

29. The module defined in claim 24 wherein said data control assembly further comprises a battery.

30. The module defined in claim 24 wherein said data control assembly further comprises a connector to receive power from a battery positioned in said housing and a battery positioned remote from said housing.

31. The module defined in claim 24 wherein said data control assembly further comprises means for measuring the temperature of said data control assembly.

32. The module defined in claim 24 wherein said data control assembly further comprises means for measuring current received from a photocell positioned remote from said housing.

33. The module defined in claim 24 wherein said data control assembly further comprises a clock.

* * * * *